United States Patent [19]

Boutevin et al.

[11] Patent Number: 5,453,528

[45] Date of Patent: Sep. 26, 1995

[54] OPTIMIZED PROCESS FOR INERT FLUORINATED SILANES

[75] Inventors: Bernard Boutevin; Francine Guida-Pietrasanta, both of Montpellier; Amedee Ratsimiehety, Montellier Cedex 1, all of France; Gerardo Caporiccio, Milan, Italy

[73] Assignee: Dow Corning Corporation, Midland, Mich.

[21] Appl. No.: 343,322

[22] Filed: Nov. 21, 1994

[30] Foreign Application Priority Data

Jun. 1, 1994 [FR] France ............................ 9406677

[51] Int. Cl.⁶ ...................................................... C07F 7/08
[52] U.S. Cl. ............................................ 556/431; 556/488
[58] Field of Search ............................ 556/431, 488

[56] References Cited

U.S. PATENT DOCUMENTS

| | | |
|---|---|---|
| 2,380,995 | 8/1945 | Rochow . |
| 2,413,582 | 12/1946 | Rust et al. . |
| 2,426,121 | 8/1947 | Rust et al. . |
| 2,426,122 | 8/1947 | Rust et al. . |
| 2,449,561 | 3/1950 | Barry . |
| 3,746,732 | 7/1973 | Atwell et al. . |
| 4,458,087 | 7/1984 | McAlister ............... 556/488 X |
| 4,481,366 | 11/1984 | Hiyama et al. ............... 556/431 |
| 4,604,477 | 8/1986 | Rich . |
| 4,692,537 | 9/1987 | McAlister ............... 556/488 X |
| 5,233,071 | 8/1993 | Wilczek ............... 556/479 |

FOREIGN PATENT DOCUMENTS

| | | |
|---|---|---|
| 0284873 | 10/1988 | European Pat. Off. . |
| 2163579 | 7/1973 | France . |
| 2260282 | 6/1973 | Germany . |
| 3531452A1 | 3/1986 | Germany . |
| 1-96187 | of 1989 | Japan . |
| 1-96186 | of 1989 | Japan . |
| 1114782 | 5/1968 | United Kingdom . |

OTHER PUBLICATIONS

Djurovich et al., Synthesis, Structure and C—H Bond Activation Chemistry of (n⁶—Arene)Ru(H)₂(SiMe₃)₂ Complexes, *Organometallics*, 13:2551–2553 (1994).

Djurovich et al., Transfer Dehydrogenative Coupling of Triethylsilane Catalysed by Ruthenium and Rhodium Complexes. A New Si—C Forming Process, *J. Chem. Soc., Chemical Communications* No. 1/000–000C, pp. 1897–1898 (1994).

Rich, Johnathon D, Silylative Decarbonaylation: A New Route to Arylsilanes. *J. Am. Chem. Soc.*, 111:5886–5893 (1989).

Sakakura et al., Catalytic C—H Activation. Silylation of Arenes with Hydrosilane or Disilane by RhCl (CO) (PMe₃)₂ under Irradation, *Chemistry Letters* 1987, pp. 2375–2378.

Seki et al., Single–Operation Synthesis of Vinylsilanes from Alkenes and Hydrosilanes with the Aid of Ru₃(CO)₁₂. *J. Org. Chem.* 1986 vol. 51, No. 20:3890–3895.

Gustavson et al., Homogeneous Activation of the C—H Bond. Formation of Phenylsiloxanes from Benzene and Silicon Hydrides. *Organometallics*, 1982 vol. 1 No. 6:884–885.

Wright, Anthony, The Role of Boron Trichloride in the Synthesis of Phenyltrichlorosilane from Benzene and Trichlorosilane. *Journal of Organometallic Chemistry* 1978 vol. 145:307–314.

Larson et al., A Convention Synthesis of Aryl Silanes from Chlorobenzenes. *Syn. React. Inorg. Metal–Org. Chem.* 1976 vol. 6 No. 1:21–29.

Barry et al., Metal–Organic Compounds: Direct Process for Preparation of Arylhalosilanes. *American Chemical Society* 1959:246–264.

Rochow et al., The Direct Synthesis of Phenylchlorosilanes. 1945, *J. Amer. Chem. Soc.* 1945, 67:1772–1774.

Rochow Eugene, The Direct Synthesis of Organosilicon Compounds. 1945, *J. Amer. Soc.* 1945, 67:963–965.

Djurovich, et al., "C—H Bond Activation and Organosilyl Functionalization Catalyzed by (n⁶—Arene)Ru(H)₂(SiR₃)₂ Complexes", XXVII Organosilicon Symposium, Mar. 18–19, 1994, Rensselaer Polytechnic Institute, Troy, New York.

Djurovich et al., "C—H Bond Activation and Functionalization Catalyzed by (n⁶—Arene)Ru(H)₂ (SiR₃)₂ Complexes", American Chemical Society Division of Inorganic Chemistry 207th ACS National Meeting, San Diego, California Mar. 13–17, 1994.

*Primary Examiner*—Paul F. Shaver
*Attorney, Agent, or Firm*—Alexander Weitz

[57] ABSTRACT

The present invention relates to an improved method for preparing a fluorinated silane having the formula $$R^1{}_4Si \qquad (I)$$

or the formula $$R^2{}_3Si(R^3SiR^4{}_2)_zR^3SiR^2{}_3 \qquad (II)$$

said method comprising reacting the corresponding halide-functional or alkoxy-functional silane with lithium aluminum hydride or sodium borohydride to form a hydride-functional silane and then reacting the latter with a vinyl-terminated fluorotelomer or an allyl-terminated fluorotelomer, wherein at least three $R_1$ of said silane (I), at least two of the $R^2$ and at least one $R^4$ of said silane (II) are selected from derivatives of fluorotelomers or fluorocotelomers, z has an average value of 0 to 4 and $R^3$ is a derivative of an alkylene-terminated telechelic divalent telomer or cotelomer.

19 Claims, No Drawings

OPTIMIZED PROCESS FOR INERT FLUORINATED SILANES

FIELD OF THE INVENTION

This invention relates to a method for preparing particular fluorinated silanes. More particularly, the invention relates to the method wherein the reactive groups on certain silanes are first converted to silicon hydride groups by reaction with lithium aluminum hydride and the silicon hydride groups are subsequently reacted with a vinyl or allyl-functional organic compound.

BACKGROUND OF THE INVENTION

Certain chemically inert, fluorinated organosilicon compounds which find utility as hydraulic fluids, release materials, lubricants and as components in greases, inter alia, are disclosed in U.S. Pat. No. 5,110,973 to Caporiccio, said patent being assigned to the assignee of the present invention and hereby incorporated by reference. The compounds taught by Caporiccio combine the desirable properties of tetraalkylsilanes and organic polymers containing fluorinated substituents and these compounds represent a new class of materials wherein a majority of the organic groups bonded to silicon are derived from alkylene-terminated telomers and/or cotelomers of selected fluoroolefins. However, the methods suggested by Caporiccio for preparing these novel compounds rely largely on the conversion of the corresponding halogen-functional perfluoroalkyl halide (iodide or bromide) to a metal (e.g., magnesium or lithium) compound. Unfortunately, these metalloorganic methods for preparing the fluorinated organosilicon compounds have been found to be relatively inefficient when the silicon atom has two or three alkyl groups attached thereto such that they do not provide a high yield of the desired, further alkylated products. For example, when an intermediate containing the structure —Si(Cl$_2$)—R$^3$—Si(Cl$_2$)—, in which R$^3$ is a divalent organic group, is reacted with a Grignard reagent of the form R$_f$MgI, in which R$_f$ is a fluorinated alkyl group, the yield is quite poor if the R$_f$ group is large. Furthermore, when each silicon atom of the intermediate is already bonded to one such R$_f$ group, as in structures of the type —Si(Cl)(R$_f$)—R$^3$—Si(Cl)(R$_f$)—, reaction with a second Grignard reagent of the form R$^2_f$MgI to add the group R$^2_f$ is still more difficult, even if the group is small and the reaction is carried out under the preferred low temperature conditions. This situation is somewhat improved when the perfluoroalkyl group is added by employing a lithium compound of the type LiR$_f$ but is still relatively inefficient. The observed yields are not much improved when the desired product is of the form R$^1_4$Si wherein R$^1$ is a monovalent group derived from a fluorotelomer or fluorocotelomer, as defined in the above cited patent to Caporiccio.

SUMMARY OF THE INVENTION

It has now been found that the fluorinated organosilicon compounds taught by Caporiccio can be produced in greater yield by carefully selecting the proper reaction sequence. In particular, it has been discovered that this yield is significantly improved when the halogen or alkoxy groups of the above described silane intermediates substituted with two or three fluoroalkyl groups are first converted to silicon hydride groups by reaction with lithium aluminum hydride or sodium borohydride and the silicon hydride groups are subsequently reacted with a vinyl- or allyl-functional fluorotelomer. Moreover, the method of the present invention allows the efficient preparation of specific novel fluorinated organosilicon compounds having surprisingly low glass transition temperatures, typically below about −45° C. and some as low as −73° C., making these compounds particularly suitable for low temperature hydraulic and lubrication applications.

The present invention therefore relates to a method for preparing a fluorinated silane having the formula

$$R^1_4Si \tag{I}$$

said method comprising:
(A) reacting a silane of the formula

$$R^1_{4-w}R^8_wSi \tag{III}$$

with lithium aluminum hydride or sodium borohydride to form a silane of the formula

$$R^1_{4-w}H_wSi \tag{V}$$

; and
(B) reacting said silane (V) with a compound selected from the group consisting of vinyl-terminated fluorotelomers and allyl-terminated fluorotelomers, wherein at least three R$^1$ of said silane (I) are selected from derivatives of fluorotelomers or fluorocotelomers, w is 1 or 2 and R$^8$ is selected from the group consisting of Cl, F and OCH$_3$ radicals.

The invention further relates to a method for preparing a fluorinated silane having the formula

$$R^2_3Si(R^3SiR^4_2)_zR^3SiR^2_3 \tag{II}$$

comprising:
(A) reacting a silane of the formula

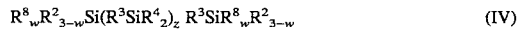
$$R^8_wR^2_{3-w}Si(R^3SiR^4_2)_z R^3SiR^8_wR^2_{3-w} \tag{IV}$$

with lithium aluminum hydride or sodium borohydride to form a silane of the formula

$$H_wR^2_{3-w}Si(R^3SiR^4_2)_zR^3SiR^2_{3-w}H_w \tag{IV}$$

; and
(B) reacting said silane (VI) with a compound selected from the group consisting of vinyl-terminated fluorotelomers and allyl-terminated fluorotelomers, wherein at least two of the R$^2$ and, when z≠0, at least one R$^4$ of said silane (II) are independently selected from derivatives of fluorotelomers or fluorocotelomers, w and R$^8$ have their previously defined meanings, z has an average value of 0 to 4 and R$^3$ is a derivative of an alkylene-terminated telechelic divalent telomer or cotelomer.

The invention also relates to species of formulas (I) and (II) prepared by the above described methods.

DETAILED DESCRIPTION OF THE INVENTION

In the above formula (I), at least three R$^1$ groups of formula (I) are monovalent radicals derived from telomers or cotelomers of fluorinated organic monomers and are independently selected from the group consisting of:
(i) alkylene-terminated monovalent homotelomers selected from the group consisting of telomers of chlorotrifluoroethylene, tetrafluoroethylene, vinylidene fluoride, and trifluoroethylene;
(ii) cotelomers selected from the group consisting of cotelomers of chlorotrifluoroethylene and hexafluoropropene;

(iii) cotelomers of tetrafluoroethylene and one member selected from the group consisting of hexafluoropropene, 1-H-pentafluoropropene and 2-H-pentafluoropropene;

(iv) cotelomers of vinylidene fluoride and one member selected from said hexa- and pentafluoropropenes;

(v) cotelomers of tetrafluoroethylene and a perfluoroalkyl vinyl ether;

(vi) cotelomers of tetrafluoroethylene, chlorotrifluoroethylene, and a perfluoroalkyl vinyl ether; and (vii) cotelomers of tetrafluoroethylene, chlorotrifluoroethylene and hexafluoropropene.

The above telomers and cotelomers are bonded to the silicon atom in the corresponding formulas (i.e., formulas I, III and V) by a divalent, linear, non-halogenated, alkylene radical containing 2, 3 or 4 carbon atoms. Any remaining $R^1$ groups in said formulas (i.e., those which are not the above described telomers or cotelomers) are independently selected from the group consisting of alkyl radicals containing from 1 to 4 carbon atoms, phenyl, perfluoroalkyl-substituted phenyl and fluoroalkyl radicals of the general formula $R^5(CH_2)_y-$ 

which $R^5$ represents a linear or branched perfluoroalkyl radical having from 1 to 6 carbon atoms and y is 2, 3 or 4. In formulas III and V, w is 1 or 2, preferably 1. In formula III, $R^8$ is selected from the group consisting of Cl, F and $OCH_3$ radicals, and is preferably F.

Likewise, in formula II, at least two of the $R^2$ groups and at least one of the $R^4$ groups are independently selected from the same telomers and cotelomers described above for group $R^1$. These telomers and cotelomers are again bonded to the silicon atoms in the corresponding formulas (i.e., formulas II, IV and VI) by a divalent alkylene radical and any remaining $R^2$ and $R^4$ groups are independently selected from the alkyl radicals, phenyl, perfluoroalkyl-substituted phenyl and fluoroalkyl radicals described in connection with formula I. In formulas IV and VI, w is 1 or 2, preferably 1. In formula IV, $R^8$ is selected from the group consisting of Cl, F and $OCH_3$ radicals, preferably F. In formulas II, IV and VI, z has an average value of 0 to 4, preferably 0 or 1, and $R^3$ is an alkylene-terminated telechelic divalent fluorinated telomer or cotelomer represented by the formula:

$-C_mH_{2m}-(R^6)CFCF_2-(C_pF_{2p})_q(C_2ClF_3)_r-R_f-(C_2ClF_3)_r-(C_pF_{2p})_q-CF_2CF(R^6)-C_mH_{2m}-$ in which $R_f$ represents a perfluoroalkylene radical containing from 2 to 6 carbon atoms, $R^6$ is fluorine or trifluoromethyl, m is 2 or 3, with the proviso that $-C_mH_{2m}-$ represents a linear radical, the value of p is 2 or 3, r is 0 or a positive integer from 1 to 6, q is 0 or a positive integer from 1 to 6 and (r+q) is from 2 to 12.

The telomers and cotelomers of the present invention are known in the art and may be prepared by the telomerization or cotelomerization of fluorine-containing monomers, said telomerization being initiated by bromo- or iodo-substituted telogens, as detailed in above cited U.S. Pat. No. 5,110,973. For example, procedures for the telomerization of tetrafluoroethylene (TFE) are well known (e.g., see Hudlicky in "Organic Fluorine Compounds", Ed. McMillan, page 347, 1962). Other procedures to obtain telomers and cotelomers used as intermediates for obtaining the silanes of the present invention are reported, for example, in the above cited patent to Caporiccio and in U.S. Pat. No. 4,731,170.

Some of the telomers and cotelomers of the present invention are preferably prepared from fluorinated iodide intermediates having 4, 6 or 8 carbon atoms (e.g., $C_4F_9I$, $C_6F_{13}I$ or $C_8F_{17}I$). These compounds are available from PCR, Inc. (Gainesville, Fla.). The telomers may also be prepared by thermal telomerization of TFE from $CF_3CF_2I$ at temperatures of 180°–250° C. using a molar ratio of $CF_3CF_2I/TFE$ of 2 to 5. The telogen and the unreacted monomer are recovered and the mixture of telomers is separated by distillation or used as a mixture for further reaction. Some of the telechelic telomer iodides of the type $I(C_2F_4)_2I$, $I(C_2F_4)_3I$ and $I(C_2F_4)_4I$ are also available from PCR, or are obtained by methods outlined in U.S. Pat. No. 4,731,170 from TFE and the telogen $IC_2F_4I$, the latter being obtained by reacting $I_2$ and TFE at 130°–160° C. The telechelic diiodo fluoro telomers may also be endcapped with hexafluoropropene (HFP) by thermal addition at 200°–240° C. to convert them to structures of the form $I(C_3F_6)_{q'}(C_2F_4)_qI$, where q=2, 3, 4; q'=1, 2.

Telomers such as $CF_3CF_2C_2F_4CF_2CF(CF_3)I$ are obtained from $C_4F_9I$ by thermal addition of HFP at 240° C. Telomers such as $C_2F_5C_2F_4(CH_2CF_2)_nCF_2CF(CF_3)I$, where n=1 or 2, are obtained from $C_4F_9I$ by thermal addition of $CH_2=CF_2$ at 200° C., followed by addition of HFP at 240° C. Telomers such as $F(CF_2-CFCl)_n CF_2CF(CF_3)I$, where n=1 to 3, are preferably obtained by thermal telomerization of CTFE using the telogen $CF_3CFClI$ at 110°–150° C. This telogen is obtained, together with $CF_2ClCF_2I$, from the addition of $IF_5$ and iodine to CTFE at 20°–100° C. Upon distilling the telomer from the unreacted $CF_2ClCF_2I$, which is inert under these conditions, the telomer of CTFE may be reacted with HFP at 180°–230° C. for the purposes of the invention. The telomer $CF_3CF(Cl)CF_2CF(CF_3)I$ is also of interest in the invention.

The above described telomers (iodo-fluorotelomers) are endcapped by groups selected from $-CH_2CH_2I$, $-CH=CH_2$, $-CH_2-CH=CH_2$ or $-CH_2CH_2CH_2I$. To obtain the endcapping by the $-CH_2CH_2I$ group, the iodo-fluorotelomers are reacted with ethylene in the presence of CuCl or CuI, also preferably in the presence of ethanolamine and solvent, such as t-butyl alcohol or acetonitrile, at 110°–180° C. according to the procedure described, e.g., by D. Burton (J. Org. Chem., 35(5), p. 1339, 1970). The 1,1,2,2 tetrahydro-1-iodo terminated fluoro telomers thusly obtained are then used to prepare Grignard reagents for the alkylation of silicon-halides according to the instant invention.

The 1,1,2,2-tetrahydro-1-iodo terminated fluorotelomers can also be transformed to the corresponding telomers having vinyl terminal groups by the well known dehydroiodination reaction using bases such as KOH in ethyl alcohol (e.g., see U.S. Pat. No. 5,110,973). The same procedure can be followed to obtain telechelic telomers of the divinyl type, such as $CH_2=CH-(C_2F_4)_nCH=CH_2$, and the like, according to the disclosure of above cited U.S. Pat. No. 5,110,973.

Allyl-terminated derivatives may be obtained, for example, by reaction of such compounds as $C_4F_9CH_2CF_2CF_2-CF(CF_3)I$ or $C_2F_5(C_2F_4)_2CF_2CF(CF_3)I$ with allyl acetate in the presence of benzoyl peroxide at a temperature of 70°–100° C. and subsequently reacting the adduct with Zn in alcoholic solvents at 25°–80° C.

According to the method of the present invention, hydrosilanes V and VI are the preferred intermediates to be used in the preparation of the products I and II, respectively, wherein the former structures are reacted with fluoro hydroolefins (vinyl or allyl terminated fluorotelomers). In this method, compound III or compound IV is preferably first obtained by reacting the telomeric or cotelomeric fluoroalkylhalide of the type $R^1X$ (X=Br or I, preferably I, and $R^1$ has its previously defined meaning) with magnesium to form a Grignard reagent. This Grignard reagent is then reacted with a silicon halide or silicon alkoxide intermediate to form the respective intermediates V and VI. This intermediate may be exemplified by such structures as: $SiCl_4$, $HSiCl_3$, $CH_3Si(OCH_3)_3$, $CF_3C_2H_4SiCl_3$, $CF_3C_2H_4Si(OCH_3)_3$, $C_6F_{13}C_2H_4SiCl_3$ (obtained by hydrosilyation of $C_6F_{13}CH=CH_2$ with $HSiCl_3$), $CH_3SiCl_2-C_2H_4C_6F_{12}C_2H_4-SiCl_2CH_3$ (prepared by hydrosilylation of $CH_2=CH-C_6F_{12}CH=CH_2$ with $CH_3Si(H)Cl_2$) and $CF_3C_2H_4SiCH_3(Cl)-C_2H_4-C_6F_{12}-C_2H_4SiCH_3(Cl)-C_2H_4CF_3$, inter alia.

When the fluoroalkyl silane III or IV is a chloride or an alkoxide (i.e., $R^8$ in III or IV is either Cl or $OCH_3$, respectively) it is preferred to convert the chloride or alkoxide to the corresponding fluoride (i.e., $R_8=F$) before reacting the fluoroalkyl silane with lithium aluminum hydride or sodium borohydride to form the hydrosilanes V or VI, as described infra. The conversion of the fluoroalkyl silane chloride or alkoxide to the corresponding fluoride is accomplished via a metathesis reaction using an aqueous-alcoholic solution of HF. This metathesis reaction is essentially quantitative and the resultant fluoralkyl silane fluorides are easily isolated as essentially 100% pure components. Additionally, these fluoroalkyl silane fluorides are non-hydrolyzable and are much more reactive with the above mentioned Grignard iodides than the corresponding fluoroalkyl silane chlorides or alkoxides. Thus, it was typically found that the Grignard alkylation of the fluoroalkyl silane showed conversions in the range of 50 to 90%.

The fluoroalkyl silane fluorides (III or IV) wherein $R_g$ is F are then reacted with $LiAlH_4$ (preferred), or sodium borohydride, in ethyl ether under reflux conditions in order to obtain the corresponding monohydro or dihydrosilane of structure V or VI, respectively, in practical quantitative yield (i.e., at least 95%).

The monohydro or dihydrosilanes (structure V or VI) are then reacted with vinyl-terminated fluorotelomers or allyl-terminated fluorotelomers according to the instant method to provide the silanes I or II, respectively. This addition reaction is facilitated by organic peroxides or, preferably, by platinum-based catalysts. Preferably, Pt supported on carbon, or more desirably as a 10–25% solution of $H_2PtCl_6 \cdot 6H_2O$ in isopropanol, is employed such that there are from $10^{-2}$ to $10^{-5}$ parts of Pt for each part of silane (molar basis). This reaction can be carried out at a temperature of 50° to 150° C., preferably at 80° to 120° C., and preferably under a partial pressure of oxygen, as is common practice in the art for such addition reactions.

Some of the preferred schemes according to the invention, but not intended to limit the scope thereof, are illustrated as follows.

Preparation of halosilane intermediates—Schemes (i)

$R^1X + Mg \rightarrow R^1MgX$ (X=Br, preferably I)
$R^1MgX + SiCl_4 \rightarrow R^1_{4-v}SiCl_v$ (v=1, 2, 3)
$R^1_{4-v}SiCl_v + HF \rightarrow R^1_{4-v}SiF_v$ (v=1, 2, 3)
$R^1MgX + HSiCl_3 \rightarrow R^1_{3-v'}-SiHCl_{v'}$ (v'=0, 1, 2)
$R^1MgX + R^1Si(OCH_3)_3 \rightarrow R^1_2Si(OCH_3)_2$
$R^1_2Si(OCH_3) + HF \rightarrow R^1_2SiF_2$ wherein $R^1$ is selected from the following groups

| | |
|---|---|
| $CF_3C_2H_4-$ | (A) |
| $C_2F_5(C_2F_4)_qC_2H_4-$ | (B) |
| $C_2F_5(C_2F_4)_qCF_2CF(CF_3)-C_2H_4-$ | (C) |
| $(CF_3)_2CFC_2H_4-$ | (D) |
| $C_4F_9(CH_2CF_2)_pCF_2-CF(CF_3)C_2H_4-$ | (E) |
| $C_4F_9(CH_2CF_2)_pCF_2-CF(CF_3)CH_2-CH_2CH_2-$ | (F) |
| $C_2F_5(C_2F_4)_q-CH_2CH_2CH_2-$ | (G) |
| $F(CF_2CFCl)_p-CF_2CF(CF^3)C_2H_4-$ | (H) | wherein q=1, 2 or 3 and p=1, 2 or 3. Thus, specific examples of the above intermediates of the type $R^1_{4-v}SiX_v$ where X=Cl, F or of the type $R^1_{3-v}SiHCl_v$, include $(B)_3SiH$; $(D)_3SiH$; $(B)_2SiX_2$; $(B)_3SiX$; $(A)(B)_2SiX$; $(A)(C)_2SiX$; $(A)(B)SiX_2$; $(B)(D)_2SiX$; and $(B)(C)_2SiX$, wherein the letters in parentheses (A), (B), (C) and (D) represent the above described examples of $R^1$ groups.

Reaction of Intermediate with Hydride Compound—Schemes (ii)

Structures of the type III, where $R^8=X=Cl$, F, are reacted with $LiAlH_4$ give structures of the form V, as defined above. Likewise, structures of the type IV (where $R^8=X=Cl$, F) are reacted with $LiAlH_4$ to give structures of the type VI.

Reaction of Hydrides with Fluoroolefins—Schemes (iii)

Hydrosilanes of the type $HSiCl_3$; type V (where w=1); type $R^1_{4-w}H_wSi$ (where w=1, 2); type VI (where w=1, 2) are reacted with fluoroolefins of the type:

| | |
|---|---|
| $CF_3-CH=CH_2$ | (L) |
| $C_2F_5(C_2F_4)_qCH=CH_2$ | (M) |
| $C_2F_5(C_2F_4)_q-CF_2CF(CF_3)CH=CH_2$ | (N) |
| $C_2F_5(C_2F_4)_q-CH_2CH=CH_2$ | (O) |
| $C_2F_5(C_2F_4)_q-CF_2CF(CF_3)CH_2-CH=CH_2$ | (P) |
| $(CF_3)_2-CF-CH=CH_2$ | (Q) |
| $F(CF_2CFCl)_pCF_2CF(CF_3)CH=CH_2$ | (R) |
| $C_2F_5(C_2F_4)_q(CH_2CF_2)_pCF_2-CF(CF_3)CH=CH_2$ | (S) |
| $C_2F_5(C_2F_4)_q(CH_2CF_2)_pCF_2-CF(CF_3)CH_2-CH=CH_2$ | (T) | wherein q=1, 2 and p=1, 2.
The resulting hydrosilanes obtained by this scheme (iii) are of the type: $(H)SiC_{13}$; (A) (B)SiH2; (A) (B)2SiH; (A) (C) 2SiH; (A) (D) 2Sill; (B) 3Sill; (B) (C) 2Sill; (B) (D) 2Sill; and (B) 2 (F) Sill, inter alia, wherein the letters in parentheses represent groups derived form the above defined fluoroolefins.

In a similar manner, the hydrides can be reacted with telechelic alpha, omega diolefins of the type:

| | |
|---|---|
| $CH_2=CH-(C_2F_4)_qCH=CH_2$ where q=, 3, 4 | (U) |
| $CH_2=CH(CF_3CF-CF_2)_p(C_2-F_4)_q CF_2-CF(CF_3)CH=CH_2$ | (W) |
| $CH_2=CH-CH_2(CF_3CF-CF_2)_p(C_2F_4)CF_2CF(CF_3)CH_2-CH=CH_2$ | (X) | where q=1, 2, 3 or 4 and p=0 or 1.
Telechelic hydrosilanes are obtained according to schemes of 15 the type (as a non-limiting example):

$CF_3C_2H_4SiH(CH_3)Cl + (U)$ (wherein q = 3) $\longrightarrow$ $CF_3C_2H_4(CH_3)(Cl)SiC_2H_4C_6F_{12}C_2H_4SiCl(CH_3)C_2H_4CF_3$ (5)

↓ HF $CF_3C_2H_4(CH_3)FSiC_2H_4C_6F_{12}C_2H_4SiF(CH_3)C_2H_4CF_3$ (10)

By hydrosilylation of said olefins from L to X with the hydrosilanes mentioned, silanes of the type I and II are obtained. Some preferred schemes are:

$(B)_3SiH+(L)\rightarrow(B)_4Si$     (c1)

$(A)(B)_2SiH+(M)\rightarrow(A)Si(B)_3$     (c2)

$(B)_3SiH+(O)\rightarrow(B)_3Si(G)$     (c3)

$(A)(C)_2SiH+(Q)\rightarrow(A)(C)_2Si\ (D)$     (c4)

$(B)(C)_2SiH+(N)\rightarrow(B)(C)_3Si$     (c5)

$(B)(C)_2SiH+(M)\rightarrow(B)_2Si(C)_2$     (c6)

$CH_3(A)(B)SiH+(M)\rightarrow(A)(B)(CH_3)SiC_2H_4C_6F_{12}$
$C_2H_4Si(A)(B)(CH_3)$     (c7)

wherein the letters in parentheses again represent the above defined groups.

Thus, by combining the above schemes type (i), (ii) and (iii) in convenient order, different final products of the type I and II can be obtained, as illustrated by the following structures:

$(C_6F_{13}C_2H_4)_4Si$
$(C_6F_{13}C_2H_4)_3Si(C_2H_4CF_3)$
$(C_6F_{13}C_2H_4)_3Si(C_3H_6C_6F_{13})$
$(C_6F_{13}C_2H_4)_3Si(C_2H_6(HFP)(VF_2)C_4F_9)$
$(C_6F_{13}C_2H_4)_2Si(C_2H_4CF_3)_2$
$(C_6F_{13}C_2H_4)_2Si(C_2H_4(HFP)C_4F_9)_2$
$(C_6F_{13}C_2H_4)Si(C_2H_4(HFP)C_4F_9)_3$
$(C_6F_{13}C_2H_4)Si(C_2H_4CF(CF_3)_2)_2(C_2H_4CF_3)$ $$CF_3C_2H_4 - \underset{\underset{R^2}{|}}{\overset{\overset{CH_3}{|}}{Si}} - C_2H_4 -\!\!\left(\!C_2F_4\!\right)_{\!\!3}\!\!- C_2H_4\underset{\underset{R^2}{|}}{\overset{\overset{CH_3}{|}}{Si}} - C_2H_4 - CF_3$$

in which $R^2 = -C_3H_6-CF(CF_3)CF_2-CF_2CH_2-C_2F_4C_2F_5$ $$CF_3C_2H_4-\underset{\underset{C_2H_4C_6F_{13}}{|}}{\overset{\overset{CH_3}{|}}{Si}} - C_2H_4-\!\!\left(\!C_3F_6\!\right)(C_2F_4)_2(C_3F_6)_{\!\!2}\!- C_2H_4\underset{\underset{C_2H_4C_6F_{13}}{|}}{\overset{\overset{CH_3}{|}}{Si}} - C_2H_4 - CF_3$$

and $CF_3CFClCF_2CF(CF_3)C_2H_4Si(C_2H_4C_6F_{13})_3$ wherein HFP represents a hexafluoropropene residue and $VF_2$ represents a vinylidene fluoride residue in the above formulae.

EXAMPLES

The following examples are presented to further illustrate the method of this invention, but are not to be construed as limiting the invention, which is delineated in the appended claims. All parts and percentages in the examples are on a weight basis and all measurements were obtained at 25° C. unless indicated to the contrary.

EXAMPLE 1

Preparation of $(C_2F_5(C_2F_4)_2C_2H_4)_4Si$

A fluorinated compound having the formula $C_2F_5(C_2F_4)_2CH=CH_2$ (obtained from PCR, Inc.) was reacted with $HSiCl_3$ at 120° C. in the presence of 200 ppm of $H_2PtCl_6.6H_2O$ in 10% solution isopropyl alcohol in a sealed glass tube into which oxygen had been introduced. After reacting for 16 hours, the product was distilled to provide a compound of the formula $C_6F_{13}C_2H4SiCl_3$ (a) with a yield of 90% (bp=85° C. at 20 torr). This silane was dissolved in ethyl ether-ethyl alcohol (1:1 by volume) and reacted with excess of 40% HF at 0° C., whereupon the mixture was poured into excess water, the ether solution collected, dried over $Na_2SO_4$ and the solvent distilled off. A product having the structure $C_6F_{13}C_2H_4SiF_3$ (b) was isolated. Silane (b) (0.1 moles) was diluted in 500 ml of anhydrous ethyl ether and added to a solution of 0.4 moles of $C_6F_{13}C_2H_4MgI$ which was prepared from $C_6F_{13}C_2H_4I$ and Mg previously activated by crystals of iodine in 0.3 molar ethyl ether solution. After 18 hours of reflux, the mixture was poured into iced 20% HCl; the ether layer was separated and washed with water. This was then treated with aqueous (40%) HF at 0° C. and the ether layer separated; the solvent was distilled and the trialkyl silane (c) was distilled at 93° C./20 torr (80% yield). This product (c) exhibited a 29Si-NMR chemical shift at +29.5 ppm (TMS).

$(C_6F_{13}C_2H_4)_3SiF$     (c)

Eighty parts of silane (c) dissolved in 150 ml of ethyl ether were added slowly to 2.8 parts of $LiAlH_4$ suspended in 150 ml of ethyl ether in a 1 liter flask equipped with a stirrer and condenser. The mixture was heated at reflux overnight, then cooled and poured into an excess of 10% HCl. The ether layer was separated, dried over $Na_2SO_4$ and distilled to give 71 parts of hydrosilane (d) (yield=95%). Analysis by 29 Si-NMR showed a shift at −2 ppm (TMS;s).

$(C_6F_{13}C_2H_4)_3SiH$     (d)

Sixty-four parts of the silane (d), 25 parts of the olefin $C_6F_{13}CH=CH_2$, 0.3 ml of a 10% solution chloroplatinic acid in isopropanol were placed in a glass tube. The tube was evacuated, then filled with oxygen (0.6 atm absolute), sealed and heated at 110° C. while stirring for 18 hours. The reaction product was recovered, filtered, distilled at 150°–160° C. (10–3 torr) from the olefin to provide 68 parts of a tetraalkyl silane (e) in 80% yield.

$(C_6F_{13}C_2H_4)_4Si$     (e)

Silane (e) showed a 29 Si-NMR chemical shift at +8.35 ppm (TMS). The viscosity of silane (e) at 25° C., as measured with a cone-plate viscosimeter, was 107 cP; at 100° C. it was 6 Cp. The specific gravity was 1.72 g/ml and the refractive index was $n^{20}{}_D=1.3301$. Considering the composition, the inert nature and the symmetry of the structure that corresponds to a very low polarity of the molecule, it was possible to predict a dielectric constant of about 2, according to the value of electronic polarization assumed to be very near to the molar polarization of the Mosotti-Clausius equation. In practical terms, a dielectric constant of 2 is characteristic of a very good insulating fluid. Analysis by DSC showed that the silane (e) had a glass transition temperature of −73° C. These properties make this silane suitable for use as a lubricant for electro-mechanical applications, as coolant for electronics and as a hydraulic fluid for aeronautics, inter alia.

(COMPARATIVE) EXAMPLE 1

An attempt was made to convert the fluorinated trialkylsilane (c) of above Example 1 to the corresponding tetraalkylsilane (e), again defined in Example 1, by reacting it with a Grignard reagent of the formula $C_6F_{13}C_2H_4$—MgI. When this reaction was carried out using diethylether, tetrahydrofuran or dibutylether, essentially no measurable conversion to the expected product was observed.

When the trialkylsilane (c) was reacted with $C_6F_{13}C_2H_4$—Li using either diethylether or dibutylether as the solvent, only a 10% yield of the product (e) was obtained.

The trialkylsilane (c) of Example 1 (0.0046 mole) was reacted with 0.15 mole of $CF_3C_2H_4$—Li (in diethyl ether; $-30°$ C./5 hours and then $20°$ C./60 hours). The yield of $(C_6F_{13}C_2H_4)_3SiC_2H_4CF_3$ (b.p.= 110°–112° C. at 0.001 torr) was 58%, still considerably less than the 80% yield obtained in the preparation of product (e) of Example 1.

EXAMPLE 2

Preparation of $(C_6F_5(C_2F_4)_2C_2H_4)_3SiC_3H_6(C_2F_4)_2C_2F_5$

An allyl derivative $C_6F_{13}CH_2$—CH=$CH_2$(a) was first prepared by adding a pure telomer $C_6F_{13}I$ (270 parts) to allyl acetate (5% in excess of stoichiometric), promoted by 1% benzoyl peroxide at 85° C. for 16 hours. The resulting fluoroalkyl acetate (70% conversion, 100% selectivity) showed 1 H-NMR chemical shifts in the region of 2.3 ppm

| (b) | $C_4F_9CF_2$ | —CF | $(CF_3)CH_2$ | $CH_2I$ | |
|---|---|---|---|---|---|
| | –118 | –183 | –74 | | (by 19 F-NMR; ppm, $CFCl_3$) |
| | | | +2.7 | +3.3 | (by 1 H-NMR; ppm, TMS) |

($CF_2CH_2$); 4.5 ppm (CHI); 4.4 ppm ($CH_2$-OAc); 2 ppm ($CH_3$). The fluoroalkyl acetate was added to a suspension of 14 parts of Zn dust in 300 ml ethanol and 2 ml HCl (36%) and heated at 50°–70° for 4 hours. This suspension was filtered and the liquid washed with HCl (5%), dried over $Na_2SO_4$, and distilled to provide the allyl derivative (a).

The allyl derivative (a) (21.7 parts) was reacted with the hydrosilane $(C_6F_{13}C_2H_4)_3SiH$ (54 parts), the latter being prepared according to the procedure of Example 1. The resulting product was distilled and a fraction (b) boiling at 170° C./$10^{-3}$ torr was obtained in 96% yield (based on the hydrosilane). This product (b) was subjected to 29 Si-NMR analysis and showed a chemical shift at +6.86 ppm (TMS); 1H-NMR showed chemical shifts in the region of 0.7–1.05 ppm ($CH_2Si$), 1.6–1.8 ppm ($CH_2CH_2CH_2$) and 1.9–2.35 ppm ($CH_2CF_2$); 19F-NMR was also consistent with the expected structure:

$(C_{2l\ F5}(C_2F_4)_2C_2H_4)_3$ SiCH$_2$CH$_2$CH$_2$(C$_{2l\ F4}$)$_2$C$_2$F$_5$     (b)

Product (b) was further analyzed and the refractive index was found to be $n^{20}_D=1.3340$ and a transition temperature of $-59°$ C. was detected by DSC.

EXAMPLE 3

Preparation of
$(C_{2l\ FB5}—C_{2l\ F4}—CF_2CF(CF_3)C_2H_4)_3$
$SiC_2H_4\ (C_{2l\ F4})_2C_{2l\ F5}$ A telomer of the structure $C_2F_5C_2F_4CF_2CF(CF_3)C_2H_4I$ (a) was prepared by adding the 204 parts of the telogen $C_2F_5C_2F_4I$ to a 500 ml Hastelloy autoclave, then adding, under vacuum, 120 parts of HFP and reacting at 210° C. for 64 hours. The HFP was recovered, the product discharged and distilled to separate the telogen from the telomer (a) (bp 45° C. at 20 torr, conversion=50%). Chemical shifts (ppm, $CFCl_3$) by 19 F-NMR for product (a) were:

| $CF_3$ | $CF_2$ | $CF_2$ | $CF_2$ | —$CF_2$ | CF | —($CF_3$)I |
|---|---|---|---|---|---|---|
| –82 | –127 | –123.7 | –121.8 | –107 | –145 | –73 |

Sixty parts of telomer (a) were charged to a 200 ml Hastelloy autoclave, which was further charged with CuCl (0.3 parts), ethanolamine (3 parts) and t-butyl alcohol (20 parts). The autoclave was sealed, evacuated, charged with ethylene gas at 35 atm. pressure and then heated at 130°–145° C. for 10 hours. The autoclave was vented and the product was poured into water and recovered by extraction with Freon™ 113. The organic layer was dried over $Na_2SO_4$, distilled and the endcapped product (b) was separated at 76° C./20 torr (conversion=90%).

$C_4F_9CF_2$—$CF(CF_3)C_2H_4I$     (b)

NMR identification of (b) was as follows:

The two reactions were repeated to provide sufficient product for subsequent reactions.

The product (b) was used to prepare a Grignard reagent as follows. A 2 liter glass flask fitted with mechanical stirrer, condenser and thermometer was charged with 0.4 g of magnesium and heated under a nitrogen flow at 100° C., then cooled and the Mg was suspended in 150 ml of anhydrous ethyl ether. A crystal of iodine was added to the stirred suspension, and then a solution of 0.24 moles of above product (b) in 650 ml anhydrous ethyl ether was added dropwise. After one hour of stirring at 30°–35° C., a solution of 0.1 mole of $C_6F_{13}C_2H_4SiF_3$, prepared according to the Example 1 and diluted in 300 ml ethyl ether was added. The mixture was refluxed for 24 hours and the final product separated and purified according to the procedure described in the Example 1. After the evaporation of the solvent the product was distilled at 120°–125° C./$2.10^{-2}$ torr to provide the silane (c) (50% yield based on the starting silane).

$(C_4F_9CF_2$—$CF(CF_3)C_2H_4)_2Si(F)C_2H_4\ C_6F_{13}$     (c)

Silane (c) was analyzed by 19 F-NMR and by 29 Si-NMR where it was characterized by a doublet centered at +28.5 ppm (TMS). The product was added to an excess of LiAlH$_4$ in 200 ml of ethyl ether and reacted according to the procedure described in Example 1. After work up, hydrosilane (d) was recovered (94% conversion). This material was characterized by I.R. spectroscopy, where it showed an adsorption at 2140 cm$^{-1}$ corresponding to SiH, and by 29

Si-NMR, where a singlet at −3.04 ppm (TMS) was observed.

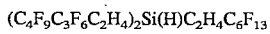 (d)

The hydrosilane (d) (0.042 mole) was reacted with 0.05 mole of $C_4F_9C_3F_6CH=CH_2$ in the presence of 0.2 ml of a 10% solution chloroplatinic acid in isopropanol. This reaction was carried out in a glass flask wherein a flow of 2% (by volume) of oxygen in nitrogen was continuously bubbled into the mixture and the latter was stirred and heated at 110° C. overnight. The crude product was filtered and distilled at 124° C./10$^{-3}$ torr, giving 38% yield of pure distilled silane (e):

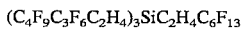 (e)

This liquid exhibited a glass transition temperature of −57° C. and a refractive index of $n^{20}_D=1.333$.

EXAMPLE 4

Preparation of

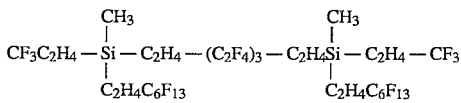

A one liter Hastelloy™ autoclave was charged, under vacuum, with 106 parts of $IC_2F_4I$ (from PCR). The autoclave was sealed and connected by a stainless steel pipe to a cylinder containing tetrafluoroethylene (TFE) gas at 7 atm pressure. The pipe was evacuated and the TFE was introduced into the autoclave. The autoclave was sealed, heated at 210° C. for 16 hours; the pressure decreased to 2 atm. The charge of TFE was repeated and the reaction continued for another 24 hours, after which the reactor was vented. Upon analysis by gas liquid chromatography (SE column), it was observed that 90% of the product comprised 5 main components. The product was distilled and 15 g of $IC_6F_{12}I$ (a) were separated, boiling at 70° C. (8–10 torr). The operation was repeated 4 times. Fifty-five grams of $IC_6F_{12}I$ were introduced into a 0.5 liter autoclave along with 0.5 g of CuI and 50 ml of t-butyl alcohol. The autoclave was sealed, evacuated and connected through a stainless steel pipe to an ethylene cylinder. Ethylene gas was introduced into the autoclave until a pressure of 35 atm was attained. The autoclave was sealed and heated at 160° C. for 16 hours, after which the autoclave was vented and a solid mixture was recovered, dissolved in hot hexane, filtered and crystallized. The resulting pure product (b) was thus isolated (conversion of 80%; identified by 19 F-NMR).

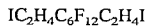 (b)

Product (b) was mixed in a glass flask, equipped with a condenser, with 15 g of KOH diluted in 100 ml of ethyl alcohol and ethylene glycol and the mixture refluxed for 3 hours. The resulting mixture was poured into excess water and the organic portion was dried over $Na_2SO_4$ and distilled. The conversion was complete and the diolefin product (c) was observed by 1H-NMR to have chemical shifts in the region 5.8–6 ppm (TMS).

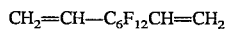 (c)

The diolefin (c) was reacted with the silane $CH_3Si(H)(C_2H_4CF_3)Cl$. This reaction was run in the presence of 50 ppm of chloroplatinic acid in a 25% solution of isopropanol at 100° C. for 16 hours, in an atmosphere of 2% oxygen (by volume) in nitrogen. The resulting liquid product (d) had the structure

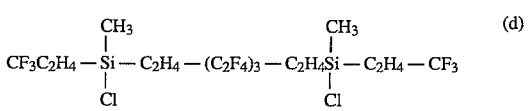

The product (d) was filtered and identified by 1H-, 19 F-, 29 Si-NMR. The characteristic 29 Si-NMR chemical shift was at 31.41 ppm (TMS) and the 1H-NMR chemical shifts were in the region of 0.52ppm, 1.04–1.09 ppm and 2.05–2.35 ppm (TMS)

Into a 250 ml flask, equipped with condenser dropping funnel, stirrer, containing $LiAlH_4$ (2 parts) suspended in anhydrous ethyl ether (50 parts), there was added dropwise 35 parts of product (d) dissolved in 100 parts of anhydrous ethyl ether. The mixture was heated at reflux for 2 hours and then treated with 10% hydrochloric acid. After separation of the ether layer and drying with sodium sulfate, the ether was distilled to yield 30.2 parts (94.6% yield) of product (e).

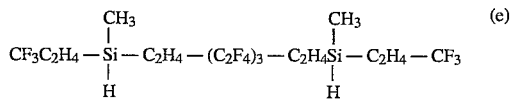

The product (e) showed I.R. adsorption at 2150 cm$^{-1}$ and 1H-NMR showed chemical shifts at 0.15; 08–1; 1.95–2.25; and 3.9–4 ppm (TMS) and 29 Si-NMR showed chemical shift at −7.22 ppm (TMS).

Into a 25 ml round-bottomed flask equipped with a condenser and a magnetic stirrer were introduced 7.02 parts of product (e), 7.6 parts of tridecafluoro-1-octene $(C_6F_{13}CH=CH_2)$ and 0.1 ml of hexachloroplatinic acid as a 10% solution in 2-propanol. The mixture was heated at 100° C. for 18 hours. Then it was filtered and vacuum distilled to eliminate any trace of olefin, to yield 13.1 parts (89.5% yield) of product (f):

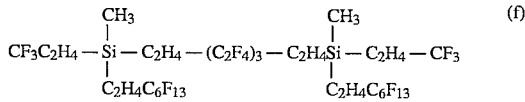

Overall yield was 84.7%.

The 1H-NMR of product (f) showed chemical shifts at 0.1– 0.15; 0.8–1; and 1.9–2.2 ppm (TMS). The 29 Si-NMR showed a chemical shift at +6.74 ppm (TMS). DSC analysis showed a glass transition temperature of −65° C.; the refractive index was $n^{20}_D= 1.3580$. It is believed that these properties would allow the product (f) of this example to be advantageously used as a lubricant for electro-mechanical application, hydraulic fluid for aeronautic applications and as a base fluid for greases.

EXAMPLE 5

Preparation of

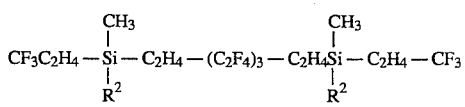

where $R^2$=—$C_3H_6$—$CF(CF_3)CF_2$—$CF_2CH_2$—$C_2F_4C_2F_5$

An allyl-terminated cotelomer of the structure $C_2FSC_2F_4CH_2CF_2CF_2$—$CF(CF_3)$—$CH_2$—$CH=CH_2$ was first prepared. Into a 500 ml Hastelloy™ autoclave equipped with mechanical stirrer were introduced 300 parts of telomer $C_2FSC_2F_4I$ (a) and 60 parts of vinylidene fluoride (VDF). The autoclave was sealed and heated at 210°–230° C., the initial pressure at 230° C. being 70 bar. After 15 hours, the reactor was cooled, the gas vented and the crude product distilled at 40° C./20 torr to provide a product (b) in 96% purity.

$$C_4F_9CH_2CF_2I \qquad (b)$$

Product (b) (290 parts) was reacted in the same autoclave with 120 parts of $C_3F_6$ (HFP) at 240° C. for 75 hours, the initial pressure at 240° being 80 bar. After venting the autoclave the crude product was distilled at 80° C./20 torr to provide 200 parts of a product (c) having a purity of 90%.

$$C_4F_9CH_2CF_2\text{—}CF_2CF(CF_3)I \qquad (c)$$

Product (c) was characterized by 19F-NMR and the chemical shifts (ppm, $CFCl_3$) found were

| $CF_3$ | $CF_2$ | $CF_2$ | $CF_2CH_2$ | $CF_2$ | $CF_2$ | $CF$ | $(CF_3)I$ |
|---|---|---|---|---|---|---|---|
| −82 | −127 | −125 | −113 | −110 | −103 | −145 | −74 |

One hundred and seventy parts of product (c) were reacted with 5% excess over the stoichiometric ratio of allyl acetate in the presence of 1% weight of benzoyl peroxide at 80° C. A conversion of 80% of adduct (d) was obtained (100% selectivity)

$$C_4F_9CH_2CF_2C_3F_6CH_2\text{—}CHI\text{—}CH_2OAC \qquad (d)$$

This adduct was characterized by 1H-NMR and showed chemical shifts similar to the acetate (a) of Example 3. To a suspension of 12 parts of Zn dust in 200 ml ethyl alcohol there was added 2 ml of 36% HCl and then 66 parts of adduct (d) were added while the temperature was maintained at 60° C. for 4 hours. Upon cooling, the resulting product was filtered, poured into excess acid water. The organic layer was recovered, dried over $Na_2SO_4$ and distilled to provide allyl derivative (e) at a conversion of 80%.

$$C_4F_9CH_2CF_2CF_2CF(CF_3)CH_2\text{—}CH=CH_2 \qquad (e)$$

The product (e) showed 1H-NMR chemical shifts of $CH_2$ in the regions of 2.7–3.1 ppm and of vinyl in the region of 5.2–5.4 ppm ($CH_2$) and 5.7–5.9 ppm (CH); 19F-NMR showed the characteristic shift of tertiary CF group at −179 ppm ($CFCl_3$).

To a 200 ml flask equipped with a condenser and magnetic stirrer, there was added 32 parts of alpha, omega-fluoroalkylene disilane (e) of Example 4, 47 parts of the allyl derivative (e) of the instant example and 0.3 ml of a 10% solution of chloroplatinic acid in 2-propanol. This mixture was heated at 100° C. for 18 hours, filtered and distilled under vacuum to provide 60 g of disilane (f) were obtained.

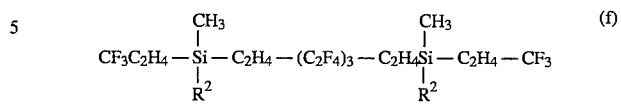

where $R^2$=—$C_3H_6$—$CF(CF_3)CF_2$—$CF_2CH_2$—$C_2F_4C_2F_5$

The 29 Si-NMR of disilane (f) showed a characteristic chemical shift at 5.27 ppm (TMS). The DSC showed a glass transition temperature of about −50° C.; the refraction index $n^{20}_D$ was 1.3640.

EXAMPLE 6

Preparation of

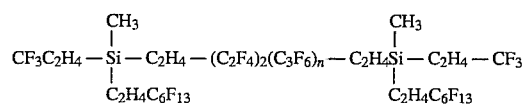

The procedures of Example 4 were used to react $IC_2F_4I$ and TFE to provide a mixture of telomers of the general formula $I(C_2F_4)_nI$ (a). This telomer mixture was distilled to give a fraction (a') boiling in the range 60°–70° C. at 20 torr with average n=2, with less than about 5% of n=3 as determined by gas chromatography and 19F-NMR analysis. One hundred parts of fraction (a') was reacted in an autoclave with 150 parts of hexafluoropropene (HFP) at 210°–230° C. for 16 hours while the pressure changed from 60 to 35 atm. After venting the autoclave the product was discharged and a fraction boiling in the range of 65°–85° C. at 10 torr and composed of about 1:1 of the components ($b^1$:$b^2$) was obtained.

$$I(C_2F_4)_2C_3F_6I \qquad (b^1)$$

$$IC_3F_6(C_2F_4)_2C_3F_6I \qquad (b^2)$$

From glc and 19F-NMR analysis, the conversion to the products ($b^1$) and ($b^2$) was about 50%.

The mixture ($b^1$, $b^2$) was reacted according to the procedures of Example 4 in the production of products corresponding to (b) to (f) of for Example 4 to provide a final fluoroalkylene disilane mixture of structure (f):

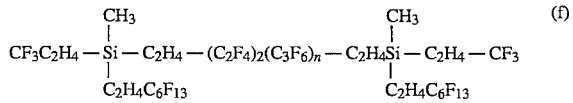

wherein n=1, 2. The compound (f) was characterized by a 19F-NMR and found to be very similar to the product (f) of Example 4, but in this case there was absorption at −180–183 ppm ($CFCl_3$) due to the CF of the groups $CF_2$—$CF(CF_3)CH_2$ of the HFP.

EXAMPLE 7

Preparation of $\{C_2F_5(C_2F_4)_2C_2H_4\}_3SiC_2H_4CF_3$

A 200 ml autoclave was charged with 69 parts of 1,1,2-tridecafluorooctene-1, 36 parts of 3,3,3- trifluoropropyldichlorosilane and 0.3 ml of a 10% solution of chloroplatinic acid in isopropanol. The autoclave was evacuated and then filled with 2% oxygen (by volume) in nitrogen, sealed and reacted at 100° C. for 16 hours. The autoclave was discharged and the product was filtered and distilled. A fraction boiling at 95°–100° C. at 1 torr was separated and analyzed by gas liquid chromatography which showed 95% of a component that, upon 29 Si-NMR evaluation, showed a chemical shift at +30.3 ppm (TMS). The 19F-NMR showed the characteristic chemical shift in agreement with the structure (a)

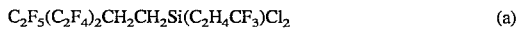

$C_2F_5(C_2F_4)_2CH_2CH_2Si(C_2H_4CF_3)Cl_2$     (a)

The above compound (a) (19.6 parts) were reacted with 2.74 parts of LiAlH$_4$ in 80 ml of anhydrous ethyl ether at reflux under nitrogen overnight. The resulting product was treated with 10% HCl at 0° C., dried and distilled at 95° C. (20 torr) to provide 14.5 parts of a product that, upon IR analysis, showed the characteristic absorption of SiH at 2150 cm$^{-1}$ and upon 29 Si-NMR analysis, showed a chemical shift at 25.6 ppm (TMS), thus confirming the structure (b)

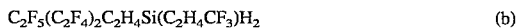

$C_2F_5(C_2F_4)_2C_2H_4Si(C_2H_4CF_3)H_2$     (b)

Product (b) (17.5 parts) was reacted overnight with 83 parts of H2C=CHC$_6$F$_{13}$ and 0.3 ml of a 10% chloroplatinic acid solution in isopropanol in a 200 ml autoclave in the presence of 2% oxygen (by volume) in nitrogen at 110°–115° C. The resulting product was filtered and distilled at 114°–120° C. (10$^{-3}$ torr) to provide a yield of 40%. Analysis by 29 Si-NMR showed a chemical shift at 7.91 ppm (TMS) and 19 F-NMR was in agreement with the structure (c).

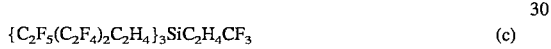

$\{C_2F_5(C_2F_4)_2C_2H_4\}_3SiC_2H_4CF_3$     (c)

The product (c) had a DSC glass transition temperature of −59° C., a refractive index of 1.3340 a viscosity of 171 cP and a density of 1.743 g/ml.

EXAMPLE 8

Preparation of $(CF_3CFClCF_2CF(CF_3)C_2H_4)Si(C_2H_4C_6F_{13})_3$

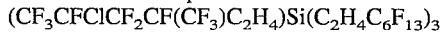

A 70/30 molar ratio of $CF_3CF(Cl)I/CF_2ClCF_2I$ (a), obtained by reaction at 20°–100° C. of chlorotrifluoroethylene (CTFE), IF$_5$ and I$_2$ in the presence of AlBr$_3$, was distilled. This mixture (16.6 parts) was introduced in a 200 ml autoclave, whereupon 30 parts of HFP were introduced under vacuum. The autoclave was sealed and heated at 250° C. for 48 hours. The reactor was cooled, vented and the liquid product distilled to obtain 20 parts of product (b) that exhibited 19 F-NMR chemical shifts as follows:

| CF$_3$ | CFCl | CF$_2$ | CFI | CF$_3$ |
|---|---|---|---|---|
| −77.5 | −130 to −134 | −101 to −107 | −141 | −73 |

Fifteen parts of the product (b) were introduced into a 200 ml autoclave along with 0.2 part of CuI in 20 ml of CH$_3$CN. The autoclave was then charged at 35 atm with ethylene gas and a reaction was carried out at 130°–150° C. while stirring overnight. The resulting mixture containing the adduct having the structure $CF_3CFClCF_2CF(CF_3)CH_2$—CH$_2$I (c) was slowly introduced through a glass tube to the bottom of a flask containing an excess of KOH in 1:1 solution of ethanol and ethylene glycol heated at 80° C. while an absolute pressure of 30–50 torr was maintained in order to distill a mixture of alcohol and olefin (d).

$CF_3CFClC_3F_6CH$=$CH_2$     (d)

The product (d), which had 1H-NMR chemical shifts in the region of 5.7 and 6.12 ppm, was reacted with a sample of the fluorotrialkyl silane (d) of the Example 1, $(C_6F_{13}C_2H_4)_3SiH$, using the reactant ratio and the procedure of Example 1, to obtain the tetralkyl silane (e), this structure being confirmed by 19 F-NMR analysis.

$(C_6F_{13}C_2H_4)_3SiC_2H_4C_3F_6CFClCF_3$     (e).

EXAMPLE 9

Preparation of

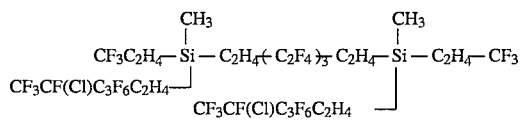

The hydrogen-functional intermediate (e) of Example 4 was reacted with $CF_3CF(Cl)C_3F_6CH$=$CH_2$ (i.e., (d) of Example 8) using the procedure described in Example 4 to produce a disilane of the structure

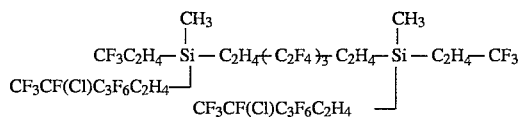

The above product was obtained in a yield of 80% and its structure was consistent with 29 Si and 19 F-NMR analysis.

EXAMPLE 10

Preparation of $(C_6F_{13}C_2H_4)_3SiC_3H_6(C_{3l\ F6})_n$ $(C_{2l\ F4})_2C_3H_6Si(C_2H_4C$ A telechelic cotelomer of the structure $CH_2$=CHCH$_2$(C$_3$F$_6$)$_n$(C$_2$F$_4$)$_2$CH$_2$CH=CH$_2$ (n=1, 2) was obtained from the components b$^1$ and b$^2$ of Example 6 according to the methods described in Example 5, steps (c) through (e). This cotelomer was reacted with $(C_6F_{13}C_2H_4)_3$SiH in a molar ratio of 1:2.2, respectively, this reaction being carried out at 100° C./18 hours in a sealed tube using chloroplatinic acid catalyst. The product, obtained in 95% yield, was a disilane of the formula: $(C_6F_{13}C_2H_4)_3SiC_3H_6(C_3F_6)_n$ $(C_2F_4)_2C_3H_6Si(C_2H_4C_6F_{13})_3$ (n=1, 2)

That which is claimed is:

1. A method for preparing a fluorinated silane having the formula

$R^1_4Si$     (I)

said method comprising:
(A) reacting a silane of the formula

$R^1_{4-w}R^8_wSi$     (III)

with a hydride compound selected from the group consisting of lithium aluminum hydride and sodium borohydride to form a silane of the formula

$R^1_{4-w}H_wSi$     (V)

; and
(B) reacting said silane (V) with a compound selected from the group consisting of vinyl-terminated fluorotelomers and allyl-terminated fluorotelomers, wherein at least three $R^1$ of said silane (I) are selected from the group consisting of derivatives of (i) alkylene-terminated monovalent homotelomers of chlorotrifluoroethylene, tetrafluoroethylene, vinylidene fluoride, or trifluoroethylene;
  (ii) cotelomers selected from the group consisting of cotelomers of chlorotrifluoroethylene and hexafluoropropene;
  (iii) cotelomers of tetrafluoroethylene and one member selected from the group consisting of hexafluoropropene, 1-H-pentafluoropropene and 2-H-pentafluoropropene;
  (iv) cotelomers of vinylidene fluoride and one member selected from said hexa- and pentafluoropropenes;
  (v) cotelomers of tetrafluoroethylene and perfluoroalkyl vinyl ether;
  (vi) cotelomers of tetrafluoroethylene, chlorotrifluoroethylene, and a perfluoroalkyl vinyl ether; and
  (vii) cotelomers of tetrafluoroethylene, chlorotrifluoroethylene and hexafluoropropene, said telomers and cotelomers (i) through (vii) being bonded to the silicon atom in formula (I) by a divalent alkylene radical having 2 or 3 carbon atoms and any remaining $R^1$ groups being independently selected from the group consisting of alkyl radicals containing from 1 to 4 carbon atoms, phenyl, perfluoroalkyl-substituted phenyl and fluoroalkyl radicals of the general formula $R^5(CH_2)_y$—, in which $R^5$ represents a perfluoroalkyl radical having from 1 to 6 carbon atoms and y is 2, 3 or 4, and wherein w is 1 or 2 and $R^8$ is selected from the group consisting of Cl, F and $OCH_3$ radicals.

2. The method according to claim 1, wherein said hydride compound is lithium aluminum hydride.

3. The method according to claim 1, wherein w of said formulas (III) and (V) is 1.

4. The method according to claim 1, wherein the $R^8$ group of said formula (III) is F.

5. The method according to claim 1, wherein said at least one $R^1$ group of said silane (I) is selected from the group consisting of $CF_3C_2H_4$—,
$C_2F_5(C_2F_4)_qC_2H_4$—,
$C_2F_5(C_2F_4)_qCF_2CF(CF_3)$—$C_2H_4$—,
$(CF_3)_2CFC_2H_4$—,
$C_4F_9(CH_2CF_2)_pCF_2$—$CF(CF_3)C_2H_4$—,
$C_4F_9(CH_2CF_2)_pCF_2$—$CF(CF_3)CH_2$—$CH_2CH_2$—,
$C_2F_5(C_2F_4)_q$—$CH_2CH_2CH_2$—,
$F(CF_2CFCl)_p$—$CF_2CF(CF^3)C_2H_4$—, wherein q=1, 2 or 3 and p=1, 2 or 3.

6. The method according to claim 5, wherein w of said formulas (III) and (V) is 1 and the $R^8$ group of said formula (III) is F.

7. A method for preparing a fluorinated silane having the formula $$R^2{}_3Si(R^3SiR^4{}_2)_zR^3SiR^2{}_3 \qquad (II)$$

comprising:
(A) reacting a silane of the formula $$R^8{}_wR^2-SiR^4)R_3SiR^8R^2{}_{3-w} \qquad (IV)$$

with a hydride compound selected from the group consisting of lithium aluminum hydride and sodium borohydride to form a silane of the formula $$H_wR^2{}_{3-w}Si(R^3SiR^4{}_2)_zR^3SiR^2{}_{3-w}H_w \qquad (VI)$$

; and
(B) reacting said silane (VI) with a compound selected from the group consisting of vinyl-terminated fluorotelomers and allyl-terminated fluorotelomers, wherein at least two of the $R^2$ and, when z≠0, at least one $R^4$ of said silane (II) is independently selected from the group consisting of derivatives of (i) alkylene-terminated monovalent homotelomers of chlorotrifluoroethylene, tetrafluoroethylene, vinylidene fluoride or trifluoroethylene;
  (ii) cotelomers selected from the group consisting of cotelomers of chlorotrifluoroethylene and hexafluoropropene;
  (iii) cotelomers of tetrafluoroethylene and one member selected from the group consisting of hexafluoropropene, 1-H-pentafluoropropene and 2-H-pentafluoropropene;
  (iv) cotelomers of vinylidene fluoride and one member selected from said hexa- and pentafluoropropenes;
  (v) cotelomers of tetrafluoroethylene and perfluoroalkyl vinyl ether;
  (vi) cotelomers of tetrafluoroethylene, chlorotrifluoroethylene, and a perfluoroalkyl vinyl ether; and
  (vii) cotelomers of tetrafluoroethylene, chlorotrifluoroethylene and hexafluoropropene;

said telomers and cotelomers (i) through (vii) being bonded to the silicon atom in formula (II) by a divalent alkylene radical having 2 or 3 carbon atoms and any remaining $R^2$ and $R^4$ groups being independently selected from the group consisting of alkyl radicals containing from 1 to 4 carbon atoms, phenyl, perfluoroalkyl-substituted phenyl and fluoroalkyl radicals of the general formula $R^5(CH_2)_y$—, in which $R^5$ represents a perfluoroalkyl radical having from 1 to 6 carbon atoms and y is 2, 3 or 4, and wherein w is 1 or 2, $R^8$ is selected from the group consisting of Cl, F and $OCH_3$ radicals, z has an average value of 0 to 4 and $R^3$ is a derivative of an alkylene-terminated telechelic divalent telomer or cotelomer represented by the formula:

$$—C_mH_{2m}—(R^6)CFCF_2—(C_pF_{2p})_q(C_2C_1F_3)_r—R_f—(C_2ClF_3)_r$$
$$—(C_pF_{2p})_q—CF_2CF(R^6)—C_mH_{2m}—$$

in which $R_f$ represents a perfluoroalkylene radical containing from 2 to 6 carbon atoms, $R^6$ is fluorine or trifluoromethyl, m is 2 or 3, with the proviso that —$C_mH_{2m}$— represents a linear radical, the value of p is 2 or 3, r is 0 or a positive integer from 1 to 6, q is 0 or a positive integer from 1 to 6 and (r+q) is from 2 to 12.

8. The method according to claim 7, wherein said hydride compound is lithium aluminum hydride.

9. The method according to claim 7, wherein w of said formulas (IV) and (VI) is 1.

10. The method according to claim 7, wherein the $R^8$ group of said formula (IV) is F.

11. The method according to claim 7, wherein at least one $R^2$ group of formula (II) is selected from the group consisting of $CF_3C_2H_4$—,
$C_2F_5(C_2F_4)_qC_2H_4$—,
$C_2F_5(C_2F_4)_qCF_2CF(CF_3)$—$C_2H_4$—,
$(CF_3)_2CFC_2H_4$—,
$C_4F_9(CH_2CF_2)_pCF_2$—$CF(CF_3)C_2H_4$—,
$C_4F_9(CH_2CF_2)_pCF_2$—$CF(CF_3)CH_2$—$CH_2CH_2$—,
$C_2F_5(C_2F_4)_q$—$CH_2CH_2CH_2$—,
$F(CF_2CFCl)_p$—$CF_2CF(CF_3)C_2H_4$—, wherein q=1, 2 or 3 and p=1, 2 or 3.

12. The method according to claim 11, wherein w of said formulas (IV) and (VI) is 1 and the $R^8$ group of said formula (IV) is F.

13. The method according to claim 7, wherein each z of said formulas (II), (IV) and (VI) is 0 or 1.

14. The method according to claim 8, wherein each z of said formulas (II), (IV) and (VI) is 0 or 1.

15. The method according to claim 9, wherein each z of said formulas (II), (IV) and (VI) is 0 or 1.

16. The method according to claim 10, wherein each z of said formulas (II), (IV) and (VI) is 0 or 1.

17. The method according to claim 11, wherein z of said formulas (II), (IV) and (VI) is 0 or 1.

18. The method according to claim 12, wherein z of said formulas (II), (IV) and (VI) is 0 or 1.

19. A fluorinated silane having a structure selected from the group consisting of $(C_2F_5(C_2F_4)_2C_2H_4)_4Si$,
$(C_2F_5(C_2F_4)_2C_2H_4)_3SiCH_2CH_2CH_2(C_2F_4)_2C_2F_5$,
$(C_4F_9C_3F_6C_2H_4)_3SiC_2H_4C_6F_{13}$,

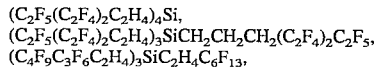

-continued

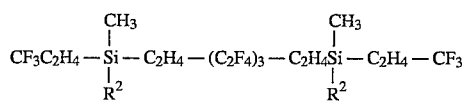

wherein $R^2 = -C_3H_6-CF(CF_3)CF_2-CF_2CH_2-C_2F_4C_2F_5$,

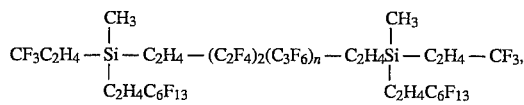

$\{C_2F_5(C_2F_4)_2C_2H_4\}_3SiC_2H_4CF_3$,
$(C_6F_{13}C_2H_4)_3SiC_2H_4C_3F_6CFClCF_3$,

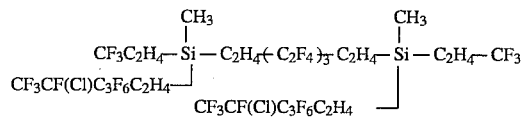

and $(C_6F_{13}C_2H_4)_3SiC_3H_6(C_3F_6)_n(C_2F_4)_2C_3H_6Si(C_2H_4C_6F_{13})_3$
where n = 1 or 2.

* * * * *